United States Patent [19]
Rogers et al.

[11] 4,329,987
[45] May 18, 1982

[54] SUBCLAVIAN INTRAVENOUS CLAMP

[75] Inventors: Thomas D. Rogers, 4211 Davis La., Chattanooga, Tenn. 37416; Rhonda J. Edmons, 7106-B Holland La., Chattanooga, Tenn. 37421; Gordon D. McBryar, Chattanooga, Tenn.

[73] Assignees: Thomas Derrill Rogers; Rhonda Joy Edmons, both of Chattanooga, Tenn.

[21] Appl. No.: 178,500

[22] Filed: Nov. 21, 1980

[51] Int. Cl.³ .............................................. A61M 5/00
[52] U.S. Cl. ................................. 128/214 R; 128/247; 285/114; 285/322
[58] Field of Search ............... 285/243, 260, 319, 322, 285/114; 128/214, 214.2, 247

[56] References Cited

U.S. PATENT DOCUMENTS

| 1,683,350 | 9/1928 | Hein | 285/322 X |
| 4,013,310 | 3/1977 | Dye | 285/322 X |
| 4,082,094 | 4/1978 | Dailey | 128/214 R |
| 4,230,109 | 10/1980 | Geiss | 128/214 R |
| 4,288,112 | 9/1981 | Stoll | 285/322 X |
| 4,296,949 | 10/1981 | Muetterties et al. | 128/214 R X |

FOREIGN PATENT DOCUMENTS 1506163  4/1978  United Kingdom ............ 128/214 R

Primary Examiner—Dalton L. Truluck
Attorney, Agent, or Firm—Alan Ruderman

[57] ABSTRACT

A clamp for preventing separation of a connected subclavian catheter and intravenous tubing has a tube-like member having internal ridges adjacent one end for gripping a resilient bulb portion of the tubing and has a series of radially moveable jaw members on the other end bendable inwardly to grasp the end of a needle head on the catheter. A lock ring positioned about the tube-like member is slideable into engagement with cam members on the jaw members to lock the latter position.

6 Claims, 5 Drawing Figures

U.S. Patent May 18, 1982 4,329,987
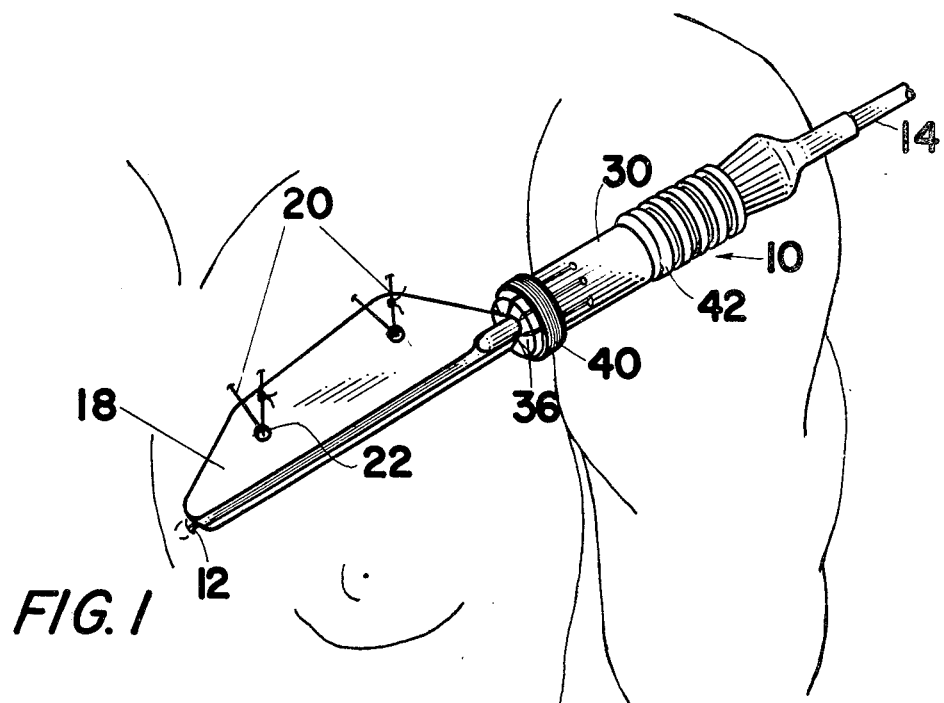
FIG. 1
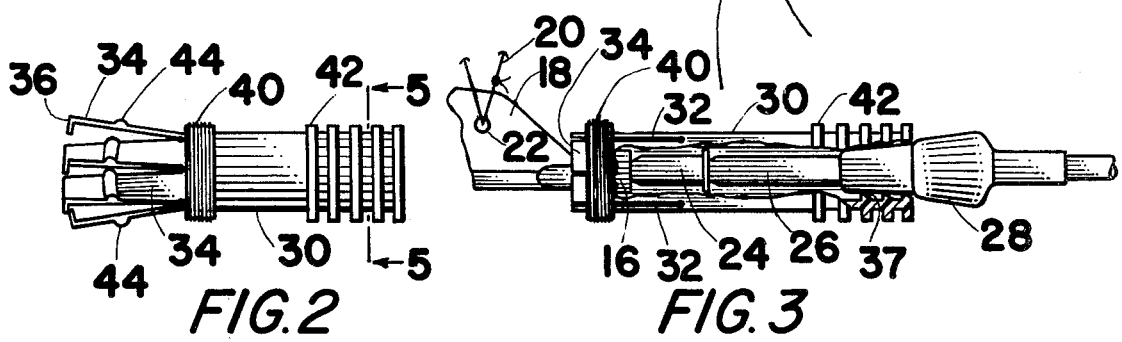
FIG. 2  FIG. 3
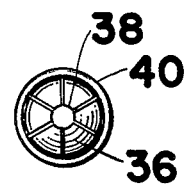 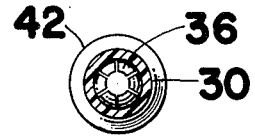
FIG. 4  FIG. 5

SUBCLAVIAN INTRAVENOUS CLAMP

BACKGROUND OF THE INVENTION

This invention relates to medical-surgical devices for connecting intravenous tubing to a catheter and more particularly to a clamping device for ensuring against separation of the connection between intravenous tubing and a subclavian catheter implanted in a patient.

During certain medical procedures it may be necessary to insert a catheter into the subclavian vein in the chest cavity to supply large amounts of medication or for intravenous feeding. Recent practice uses a catheter needle assembly in which a long flexible catheter is telescopically received concentrically within the needle. The needle is inserted into the vein and the catheter is threaded through the needle, the needle thereafter being withdrawn and held in a clamp secured to the patient with the head of the needle positioned outside the clamp. An intravenous tube receiving socket or receptacle is formed on the end of the catheter and extends outside the needle head remote from the inserted portion for receiving a plug-like insert formed on the end of the intravenous tubing adjacent a bulbous portion, the socket and insert being connected by a friction fit. Although this connection serves its purpose when no separating force is applied to the catheter or tubing, separating difficulties are encountered when a patient in an unconscious or semiconscious condition flails about and pulls at the apparatus. Because a pressure change occurs in the subclavian vein during the breathing process, if a separation occurs between the catheter and the intravenous tubing, air can be sucked into the catheter resulting in an air embolus with grievous injury or death befalling the patient.

SUMMARY OF THE INVENTION

Consequently, it is a primary object of the present invention to provide a clamp for securing the intravenous tubing to the subclavian catheter to minimize the risk of air entering the catheter.

It is another object of the present invention to provide a clamping device for preventing separation of the connection between a subclavian catheter and intravenous tubing.

It is a further object of the present invention to provide a clamping member for positively gripping the adjoining ends of a subclavian catheter and the cooperatively connected intravenous tubing to ensure against separation thereof.

To attain these objectives the present invention provides a clamp for preventing relative axial movement of the subclavian catheter and the intravenous tubing to maintain the connection fast at the adjoining ends. The clamp comprises a tube-like member having internal ridges or ribs adjacent one end thereof and a plurality of radially moveable jaw members on the other end, the jaw members being moveable inwardly toward the axis of the tube from an inoperative position toward a clamping position and locked in the latter position by a lock ring which may act against cooperating camming members on the jaw members. The clamp is positioned about the intravenous tubing with the ridges in gripping engagement with a resilient bulbous portion of the tubing adjacent the terminal plug-like insert, the latter extending substantially axially toward the end of the clamp carrying the jaw members. Thereafter the clamp is positioned about the catheter needle head and socket, the latter being forced into connecting engagement with the plug-like insert, and the jaw members are closed about the needle head and secured by the lock ring. The jaws are formed with radial and circumferential portions, the radial portion being disposed to act against the catheter facing end of the needle head to prevent relative axial movement thereof while the circumferential portions act against the surface of the needle head to prevent relative radial movement thereof.

BRIEF DESCRIPTION OF THE DRAWINGS

The particular features and advantages of the invention as well as other objects will become apparent from the following description taken in connection with the accompanying drawings, in which:

FIG. 1 is an isometric view illustrating a clamp constructed in accordance with the principles of the present invention in the operative position securing a subclavian catheter to intravenous tubing, the catheter being depicted diagrammatically as implanted within a patient;

FIG. 2 is a side elevational view illustrating the clamp shown in FIG. 1 in the inoperative or unlocked position;

FIG. 3 is a view similar to FIG. 2 but illustrating the operative locked position of the clamp with parts thereof broken away for purposes of illustration;

FIG. 4 is an end view of the clamp as viewed from the left end of FIG. 2 but in locked condition; and FIG. 5 is a cross sectional view taken substantially along line 5—5 of FIG. 2.

DESCRIPTION OF THE PREFERRED EMBODIMENT

Referring now to the drawings a clamp constructed in accordance with the principles of the present invention, illustrated generally at 10, is shown in the operative position in conjunction with a conventional subclavian catheter 12 implanted within the subclavian vein of a patient and with intravenous tubing 14 through which medication or nutritious feeding matter is fed to the catheter. The catheter is received telescopically within a needle having a metal cylindrical needle head 16 at the end remote from the catheter, the needle in the operative position being held stationary within a foldable clamping device 18 secured to the patient by stitches 20 passing through holes 22 in the clamping device. The needle head has a planar surface at the needle end and the needle extends axially therefrom. A plastic cylindrical socket member 24 extends from the needle head for frictionally receiving a plug-like insert 26 at the end of the intravenous tubing. Intermediate the plug-like insert and the tubing proper is a resilient bulbous member 28 conventionally formed integral with the tubing and the insert. The bulbous member 28 generally is formed from latex or other rubber-like material and may be readily compressed radially. Conventionally, the insert 26 is forced into the socket 24 and is held in place merely by frictional engagement of the plastic material from which they are formed. However, it has been found that separation can readily occur inadvertently when a patient flails about with the result that an air embolus can occur.

The clamp of the present invention prevents separation of the catheter assembly from the intravenous tubing by securely grasping the bulbous portion of the tubing and the needle head radially and by providing an axial engagement or stop against the needle head to prevent relative movement of the needle head and the tubing. To this end the clamp comprises a substantially tubular member 30 of a length substantially equal to the distance from the needle head adjacent the needle proper to the bulbous portion of the intravenous tubing preferably proximate the medial portion thereof. Formed on the interior wall of the clamp adjacent the opening receiving the intravenous tubing is at least one and preferably a plurality of ridges or ribs 37. Each of the ridges preferably has a sloped surface extending rearwardly from a maximum extention so as to form gripping teeth for engaging the bulbous portion of the intravenous tubing, the slope providing for ease of receiving the bulbous member while providing resistance against ready removal thereof from the clamp. As best illustrated in FIG. 5 the gripping ridges may extend completely about the circumference of the interior wall of the tubular clamp, but it should be understood that equivalent results would be attained if the ridges extended only partly about the circumference sufficient to provide gripping engagement with the bulbous portion.

At the forward end of the clamp, that end being the end that clamps the needle head, the tubular member has a plurality of longitudinally extending slits 32 at space locations about the periphery thereof so as to form a plurality of spaced flaps 34. The material from which the tubular member is constructed should be a readily bendable plastic such as polypropylene so that each of the flaps 34 will in effect be connected to the main body of the tubular member by a living hinge. Thus each flap can be bent outwardly away from the axis of the tubular member so that the needle head may be received within its annulus. At the free end of each of the flaps is a tab 36 having a substantially triangulated configuration such that it forms the sector of a circle. As best illustrated in FIG. 4 each of the tabs 36 has an arcuate surface 38 remote from the flaps so that when the flaps are bent equally toward the axis of the tubular member the arcuate surfaces 38 form a small circle, the radius of the circle being smaller than the radius of the needle head 16 such that the flaps can encapsulate the needle head with the tabs 36 engaging the planar surface of the needle head remote from the socket member 24. When so positioned about the connected catheter socket 24 and intravenous tubing insert 26 these members are prevented from separation by locking the flaps 34 against outward movement.

To lock the flaps once positioned about the needle head so that the tabs, which effectively act as jaws, retain the connection against axial movement the present invention proposes a lock ring 40 which is positioned about the tubular member intermediate the flaps and a plurality of annular manual gripping ribs 42 on the exterior of the tubular member at the intravenous tubing end. By providing a camming arrangement between the ring and the flaps the ring will force the flaps into locking engagement with the needle head. To this end the present invention proposes a protuberance 44 on the outer surface of each of the flaps, the protuberance of each flap being substantially equally spaced from the tabs so that the ring 40, which also is constructed of a plastic material, can be manually forced over the annular ridge provided by the totality of the protuberances and bend the flaps about the living hinges radially inwardly. Equivalent structure may be provided by providing a taper on the ring 40 or by flaring the flaps diametrically from the living hinge connection with the tubular member and the jaw end.

To use the clamping device the tubular member is placed about the insert end of the intravenous feeding while the flaps are in the open position and the ridges 37 are forced to bite into the bulbous portion of the intravenous tubing. The tube 30 is disposed about the needle head 16 and the plug-like insert 26 is inserted into the socket 24. The locking ring 40 is then pulled toward the catheter over the camming protuberances 44 forcing the jaws downwardly about the end of the head of the needle. The catheter assembly and the intravenous tubing are thusly secured and clamped together and substantially prevented from separation.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention what is claimed herein is:

1. A clamp for securing the connection of one end of a subclavian catheter assembly to a cooperating end of intravenous tubing, said intravenous tubing having an elongated plug-like insert at the connection end and a bulbous portion adjacent thereto, and the catheter assembly having a substantially cylindrical needle head with an intravenous socket at the connection end for frictionally receiving said plug-like insert, the other end of the needle head having a substantially planar surface radially spaced from a central portion, said clamp comprising a substantially elongated tubular member of finite length positioned about the connecting ends of the catheter assembly and tubing, said clamp having an internal wall, rib means formed on said wall adjacent the intravenous end thereof at least partly about the circumference a distance sufficient for gripping the surface of said bulbous portion, a plurality of circumferential spaced flap means formed on said tubular member at the other end thereof and defined between elongated slots spaced about the circumference, each of said flap means being radially bendable relative to the surface of said tubular member, jaw means formed on the free end of each flap means extending radially toward the axis of said tubular member for engaging said substantially planar surface of said needle head, and locking means for bending said flap means radially toward the axis of said tubular member into engagement with the needle head and for retaining said flap means in such engagement.

2. A clamp as recited in claim 1, wherein said locking means comprises an annular member disposed about said tubular member and axially moveable relatively thereto, and camming means for acting between said annular member and said flap means forcing said flap means radially inwardly when said annular member is axially moved toward said jaw means.

3. A clamp as recited in claim 2, wherein said camming means comprises a protuberance on said flap means.

4. A clamp as recited in claim 1, wherein said rib means comprises a plurality of axially spaced ridges.

5. A clamp as recited in claim 1, wherein each of said flap means is joined to said tubular member by a living hinge.

6. A clamp as recited in claim 4, wherein said ridges have sloped surfaces extending from a maximum elevation relatively to said wall toward the intravenous tubing.

* * * * *